United States Patent [19]

Carpenter et al.

[11] Patent Number: 4,947,828
[45] Date of Patent: Aug. 14, 1990

[54] ENDOSCOPE CONNECTOR

[75] Inventors: George J. Carpenter, Southbridge, Mass.; Walter P. Siegmund, Windham, Conn.; John M. Smith, Southbridge, Mass.

[73] Assignee: Schott Fiber Optics, Southbridge, Mass.

[21] Appl. No.: 338,900

[22] Filed: Apr. 17, 1989

[51] Int. Cl.$^5$ .............................................. A61B 1/06
[52] U.S. Cl. ......................................................... 128/6
[58] Field of Search ................................... 128/4, 6, 7

[56] References Cited

U.S. PATENT DOCUMENTS 4,586,491 5/1986 Carpenter ............................... 128/6
4,807,595 2/1989 Hiltebrandt ............................ 128/4

Primary Examiner—William H. Grieb
Attorney, Agent, or Firm—Bachman & LaPointe

[57] ABSTRACT

Piggyback endoscopes are disclosed which are connected together releasably where the scopes receive illumination from a single light source via a single fiber optic bundle which has been divided into at least two branches, one branch being individual to each scope.

16 Claims, 2 Drawing Sheets

ENDOSCOPE CONNECTOR

BACKGROUND OF THE INVENTION

The present invention relates to endoscopes and relates, in particular, to the use of two or more scopes in tandem or in "piggyback" fashion.

A prior art patent disclosing and describing such an endoscope arrangement bears U.S. Pat. No. 4,586,491 issued May 6, 1986 to George J. Carpenter entitled Bronchoscope With Small Gauge Viewing Attachment.

While the device of the '491 patent shows a piggyback arrangement and each scope includes a light guide or fiber optic light bundle, there is no disclosure of the method and means for transmitting light from a single source to the respective scopes.

SUMMARY OF THE INVENTION

Consequently, it is a special feature of the present invention to provide a method and a means for providing illumination to the distal ends of at least two endoscopes employed together in a cooperative mode from a single light source.

It is a further feature of the invention to provide a connector means for securing at least two endoscopes together in separable fashion so that when connected the scopes are fixed relative to one another.

A further feature of the invention is the utilization of the connector means as a light conduit or housing for light guide fiber optic bundles for transmitting light from a single source to each scope.

A further feature of the invention is the provision of light guide inlets of uniform configuration on each scope and on the connector means so that the inlets are standardized whereby each scope can be illuminated individually or in conjunction with one another, as desired.

A further feature of the invention deals with dividing the light guide fiber optic bundle into at least two branches within the connector means whereby one branch serves one scope and the other branch serves another scope.

A still further feature of the invention is the provision of keys and cooperating keyways or key slots on the connector means outlets and the scope light guide inlets to block relative motion between scopes when joined by the connector means.

A further feature of the invention involves a method of arranging a light guide fiber optic bundle, within a bundle housing, into at least two branches and directing each branch individually to a first scope (parent scope) and to a second scope (companion scope) wherein illumination is supplied from a single light source.

A further feature of the invention is the provision of at least two scopes each having a separate control handle means and each having separate flexible shafts with channel means in one scope for receiving the shaft of the other. Connector means joining the control handle means rigidly but in releasable fashion whereby an operator can manipulate both instruments with one hand leaving the other hand free to conduct related activities, i.e. feed the shaft of the companion scope into and through said channel means of the parent scope.

It is anticipated that the method and apparatus of the present invention will find utility in medical, veterinary and industrial applications.

An apparatus embracing certain features of the present invention may comprise, in combination, a primary or parent endoscope including a first control handle and a cooperating first shaft means, a secondary or companion endoscope including a second control handle and a cooperating second shaft means, connector means joining the first and second control handles releasably and light means having a single light source for illuminating the first and second shaft means wherein the connector means provides a housing including individual conduits directing illumination to each scope, simultaneously.

A method embracing certain other principles of the present invention which can be practiced to supply illumination to two or more scopes originating from a single light source may comprise the steps of providing a single light source, providing a light transmission means, dividing the light transmission means into at least two branches and connecting one branch to each endoscope individually whereby each scope is illuminated from said single light source.

Other features and advantages of the present invention will become more apparent from an examination of the succeeding specification when read in conjunction with the appended drawings, in which;

DETAILED DESCRIPTION OF THE PREFERRED EMBODIMENT

Figure 1:
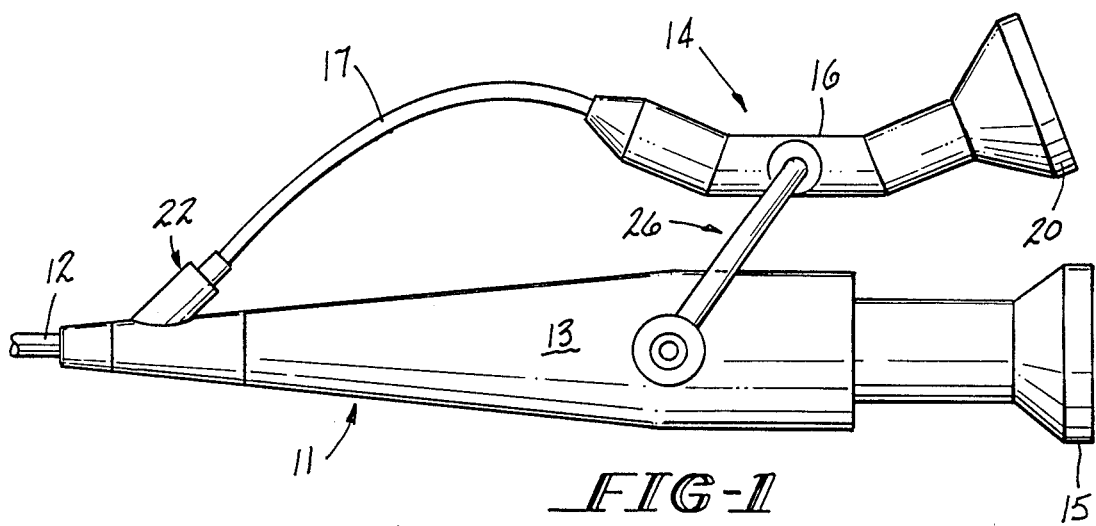
FIG. 1 is a side view of a parent endoscope and a companion endoscope connected together at the control handles.
Figure 2:
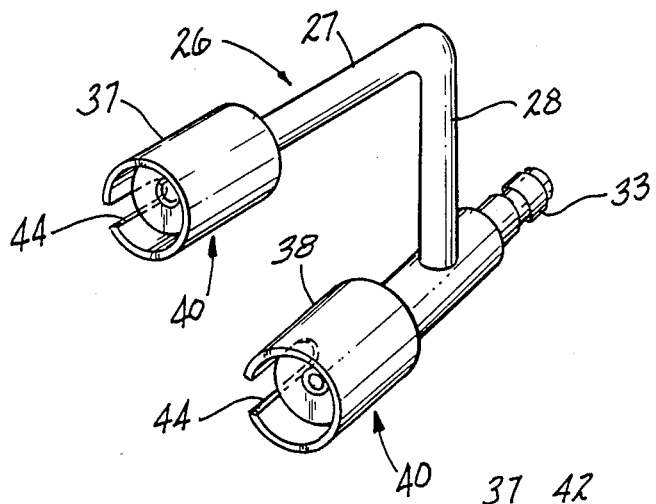
FIG. 2 is a perspective view of the endoscope connector means.
Figure 3:
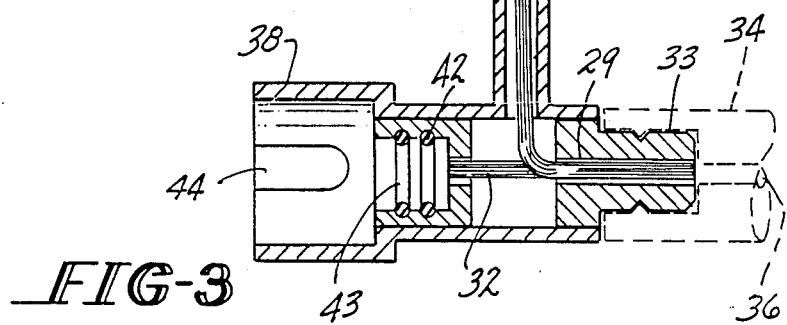
FIG. 3 is a sectional view of the connector means.
Figure 4:
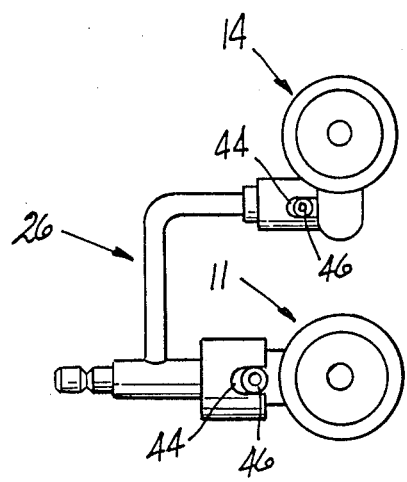
FIG. 4 is an end view of the right end of FIG. 1 showing schematically the connector mean locked to the parent and companion scopes.
Figure 5:
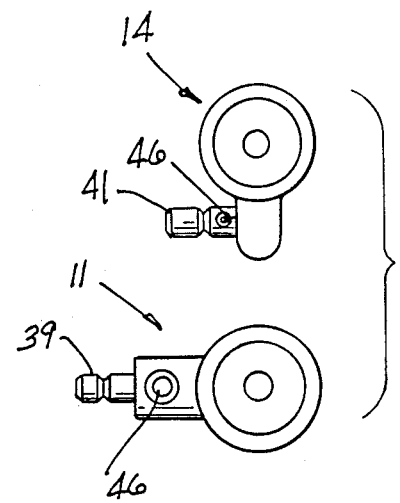
FIG. 5 is similar to FIG. 4 with the connector means removed.

Referring to FIG. 1, the reference numeral 11 designates a parent, primary or first endoscope having a first flexible shaft 12 and a first control unit 13, including eyepiece 15. Carried by the primary scope 11, in piggyback fashion, is a companion or secondary endoscope 14 having a second control unit 16 and a second flexible shaft 17 including eyepiece 20

Figure 6:
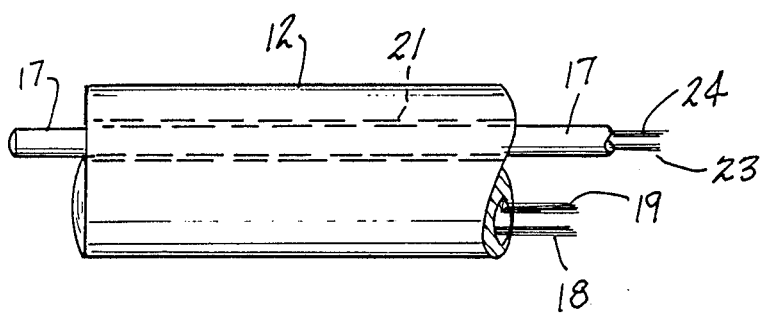
FIG. 6 shows the distal ends of the parent and companion scope shafts when in the piggyback mode.

The shaft 12 of the primary scope 11 includes the usual and customary channels for fiber optic light and image bundles 18 and 19, respectively, (FIG. 6) including a channel 21 having an inlet at 22 for receiving the second flexible shaft 17 having a light guide bundle 23 and an image bundle 24.

As is most apparent in FIG. 1, the parent scope 11 and companion scope 14 are rigidly but releasably connected by a connector means indicated generally by the reference numeral 26 facilitating holding both scopes in tandem by grasping one scope, such as the parent scope 11, in one hand fashion leaving the other hand free for other related activities such as feeding the flexible shaft 17 into channel inlet 22.

The connector means 26 having tubular arms 27 and 28, provides a housing or conduit for a fiber optic light guide or light bundle 29 divided into two branches 31 and 32. The light bundle 29 is large enough so that when it is divided into branches 31 and 32 each scope receives ample illumination. Connector means inlet 33 makes a quick operating releasable connection with socket 34 communicating with a single light source 36.

The respective light guide branches 31 and 32 terminate at outlets 37 and 38 and mate, releasably, with light guide inlets 39 and 41 on the scopes 11 and 14, respectively.

The mating outlets 37-38 and inlets 39-41 include locking means 40 in the form of O-rings 42 and circular snap rings 43 facilitating quick attachment and quick release.

To insure that the respective scopes do not move relative to one another when connected releasably by said connector means 26, each locking means 40 includes a key slot 44 and a cooperating key or lug 46.

It is to be noted that the light guide inlets 39-41 of the scopes 11 and 14 and the inlet 33 of the connector means 26 are all of uniform or standard configuration so that each scope 11 and/or 14 can be operated separately and individually, if desired, by merely making a light source connection directly to the respective light guide inlets 39 and 41 in the usual and customary fashion.

As stated earlier, the present invention contemplates a method of utilizing a single light source servicing a single light guide which in turn provides illumination to at least two separate endoscopes by dividing the single light guide fiber optic bundle into at least two branches whereby each branch services a mating scope individually.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. In combination, a plurality of endoscopes comprising:
   a primary or parent endoscope including a first control handle and a cooperating first shaft means,
   a secondary or companion endoscope including a second control handle and a cooperating second shaft means,
   connector means joining the first and second control handles, and
   light means having a single light source for illuminating said first and second shaft means, said connector means providing a housing for said light means.
2. The combination of claim 1 in which each control handle includes a light guide inlet.
3. The combination of claim 2 in which the connector means is a rigid member and includes light guide outlet connectors mating with said light guide inlets.
4. The combination of claim 3 in which said light guide inlets and outlets are separable and quick operating.
5. The combination of claim 2 in which said connector means includes at least one light guide inlet communicating with a source of light.
6. The combination of claim 5 in which all light guide inlets are of uniform configuration.
7. The combination of claim 1 in which the light means is bifurcated in said connector means to facilitate servicing each shaft means.
8. The combination of claim 1 in which the light means defines a fiber optic bundle.
9. The combination of claim 8 in which the fiber optic bundle is bifurcated in said connector means to facilitate servicing each shaft means.
10. The combination of claim 3 in which the connector means light outlets and the first and second control handle light inlets are formed with cooperating, separable locking means, said locking means comprising a key slot formed on one of each said outlet and each said inlet and a cooperating lug formed on the other of each said outlet and each said inlet whereby said first and second control handles are fixed relative to one another when connected together.
11. The combination of claim 10 in which the locking means includes seal means and friction means.
12. The combination of claim 1 in which the first control handle is formed with a channel opening for receiving the second shaft means.
13. A method of supplying at least two endoscopes each having a flexible shaft with illumination from a single light source comprising the steps of:
    providing a single light source,
    providing light transmission means,
    dividing the light transmission means into at least two branches, and
    connecting one branch to each endoscope individually whereby each endoscope is illuminated by means of said single light source.
14. The method of claim 13 in which the light transmission means is a fiber optic bundle.
15. The method of claim 13 plus the steps of providing connector means for connecting said endoscopes together releasably and dividing the light transmission means within the connector means.
16. The method of claim 13 plus the step of providing a channel inlet in one endoscope for receiving the shaft of the other endoscope.

* * * * *